(12) United States Patent  
Choi et al.

(10) Patent No.: US 7,993,810 B2
(45) Date of Patent: Aug. 9, 2011

(54) (METH)ACRYLATE COMPOUND HAVING AROMATIC ACID LABILE GROUP, PHOTOSENSITIVE POLYMER, RESIST COMPOSITION, AND ASSOCIATED METHODS

(75) Inventors: Sang-Jun Choi, Seoul (KR); Youn-Jin Cho, Anyang-si (KR); Seung-Wook Shin, Uiwang-si (KR); Hye-Won Kim, Uiwang-si (KR)

(73) Assignee: Cheil Industries, Inc., Gumi-si Kyeongsangbuk-do (KR)

( * ) Notice: Subject to any disclaimer, the term of this patent is extended or adjusted under 35 U.S.C. 154(b) by 201 days.

(21) Appl. No.: 12/314,828

(22) Filed: Dec. 17, 2008

(65) Prior Publication Data

US 2009/0170029 A1  Jul. 2, 2009

(30) Foreign Application Priority Data

Dec. 17, 2007 (KR) .................. 10-2007-0132696

(51) Int. Cl.
*G03C 7/30* (2006.01)
*G03F 7/039* (2006.01)
*C08F 20/18* (2006.01)

(52) U.S. Cl. .................. 430/270.1; 430/272.1; 430/326; 430/330; 430/311; 430/322; 560/221; 526/270; 526/266

(58) Field of Classification Search .................. None
See application file for complete search history.

(56) References Cited

U.S. PATENT DOCUMENTS

| | | | |
|---|---|---|---|
| 4,473,690 A * | 9/1984 | Yuki et al. | 526/265 |
| 4,554,323 A * | 11/1985 | Yuki et al. | 525/272 |
| 5,688,628 A * | 11/1997 | Oie et al. | 430/176 |
| 5,723,253 A | 3/1998 | Higashino et al. | |
| 5,897,811 A * | 4/1999 | Lesko | 252/301.35 |
| 6,309,790 B1 | 10/2001 | Jung et al. | |
| 6,919,157 B2 * | 7/2005 | Niwa et al. | 430/270.1 |
| 7,147,984 B2 * | 12/2006 | Yukawa et al. | 430/270.1 |
| 2002/0076641 A1 * | 6/2002 | Choi et al. | 430/270.1 |
| 2003/0232274 A1 * | 12/2003 | Barclay et al. | 430/270.1 |
| 2004/0009429 A1 * | 1/2004 | Sato | 430/287.1 |
| 2007/0184648 A1 | 8/2007 | Yoon et al. | |

FOREIGN PATENT DOCUMENTS

| | | |
|---|---|---|
| JP | 02-187763 A | 7/1990 |
| JP | 09-068798 A | 3/1997 |
| JP | 11-263749 A | 9/1999 |
| JP | 2000-264921 A | 9/2000 |
| KR | 10-2002-0002944 A | 1/2002 |
| KR | 10-0703007 B1 | 3/2007 |
| WO | WO 2007/110387 A1 | 10/2007 |

OTHER PUBLICATIONS

Nakahira et al, Macromol. Chem., Rapid Commun. 1, 437-442 (1980).*
Nakahira et al, Macromolecules, 1983, vol. 16, pp. 297-302.*
Stolka, Macromolecules, vol. 8, No. 1, Jan.-Feb. 1975, pp. 8-9.*
Ito et al, Journal of Polymer Science; Part A; Polymer Chemistry, vol. 33, pp. 137-142, year 1995.*
Iwatsuki et al, Makromol. Chem. vol. 179, pp. 189-199, year 1978.*
Simionescu et al, Journal of Polymer Science; Polymer Chemistry Edition. vol. 23, pp. 2089-2098, year 1985.*
Ferreira et al "Choice of Amines as Stabilizers for Chemically Amplifed Resist Systems", Proc. SPIE, vol. 333, pp. 236-244, year 1998.*

* cited by examiner

*Primary Examiner* — Cynthia Hamilton
(74) *Attorney, Agent, or Firm* — Lee & Morse, P.C.

(57) ABSTRACT

A (meth)acrylate compound having an aromatic acid-labile group, the (meth)acrylate compound being represented by the following Formula 1:

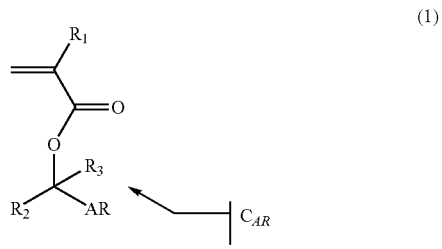

(1)

In Formula I, $R_1$ is hydrogen or methyl, $R_2$ is hydrogen, a substituted or unsubstituted alkyl, or a substituted or unsubstituted aryl, $R_3$ is hydrogen, a substituted or unsubstituted alkyl, or a substituted or unsubstituted aryl, AR is a substituted or unsubstituted phenyl, or a substituted or unsubstituted aryl having from two to four fused aromatic rings, and carbon $C_{AR}$ is bonded directly to an aromatic ring of AR.

15 Claims, 6 Drawing Sheets

Formula 1:

Formulae (a)-(i):

(a)

(b)

(c)

(d)

(e)

(f)

(g)

(h)

(i)

Formula 2:

Formula 3:

Formula 4:

Formula 5:

Reaction Scheme 1:

Reaction Scheme 2:

Reaction Scheme 3:

Reaction Scheme 4:

Formula 6:

Formula 7:

Formula 8:

(METH)ACRYLATE COMPOUND HAVING AROMATIC ACID LABILE GROUP, PHOTOSENSITIVE POLYMER, RESIST COMPOSITION, AND ASSOCIATED METHODS

BACKGROUND OF THE INVENTION

1. Field of the Invention

Embodiments relate to a (meth)acrylate compound having an aromatic acid labile group, a photosensitive polymer, a resist composition, and associated methods.

2. Description of the Related Art

For a photoresist material used to produce fine patterns, a deep-UV (deep UV) resist material using a shorter wavelength such that provided by an ArF excimer laser (193 nm) may be preferred to a resist material using a longer wavelength such as that provided by a KrF excimer laser (248 nm). For example, forming a semiconductor device with a capacity of more than 16 gigabytes needs a pattern size of less than 70 nm according to a design rule. As a result, a resist film may be thinner and have a reduced process margin for underlayer etching. The most representative problem is dry etching resistance of a photosensitive resin.

SUMMARY OF THE INVENTION

Embodiments are therefore directed to a (meth)acrylate compound having an aromatic acid labile group, a photosensitive polymer, a resist composition, and associated methods, which substantially overcome one or more of the problems due to the limitations and disadvantages of the related art.

It is therefore a feature of an embodiment to provide a (meth)acrylate compound having an aromatic acid labile group, a photosensitive polymer, a resist composition, and associated methods, which may be particularly useful in photoresist applications for lithographic processes in the 193 nm wavelength region or shorter.

At least one of the above and other features and advantages may be realized by providing a (meth)acrylate compound having an aromatic acid-labile group, the (meth)acrylate compound being represented by the following Formula 1:

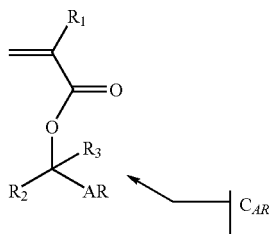

(1)

In Formula 1, $R_1$ may be hydrogen or methyl, $R_2$ may be hydrogen, a substituted or unsubstituted alkyl, or a substituted or unsubstituted aryl, $R_3$ may be hydrogen, a substituted or unsubstituted alkyl, or a substituted or unsubstituted aryl, AR may be a substituted or unsubstituted phenyl ring, or a substituted or unsubstituted aryl having from two to four fused aromatic rings, and carbon $C_{AR}$ may be bonded directly to an aromatic ring of AR.

AR may include first and second aromatic rings, the first and second aromatic rings being fused together, the first aromatic ring may have a group $R_4$ that is hydrogen, a halogen, an alkyl, or an alkoxy, and the second aromatic ring may have a group $R_5$ that is hydrogen, a halogen, an alkyl, or an alkoxy.

At least one of $R_2$ and $R_3$ may be an alkyl, an alkyl having an alkoxy substituent, an aryl, or an aryl having an alkoxy substituent.

The (meth)acrylate compound may be represented by one of the following structures (a), (b), or (d):

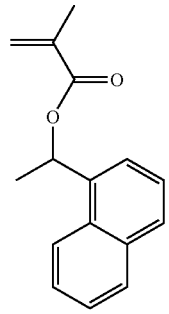

(a)

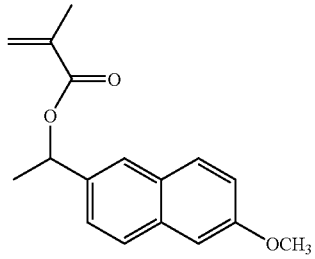

(b)

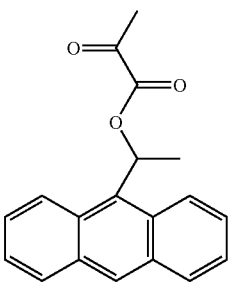

(d)

The (meth)acrylate compound may be represented by one of the following structures (c), (e), (f), (g), (h), or (i):

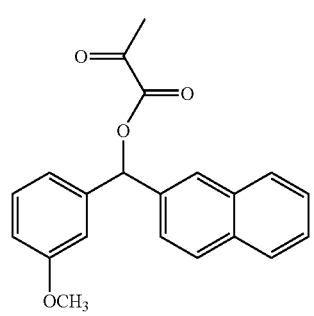

(c)

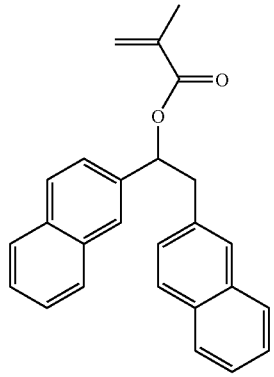

(e)

-continued

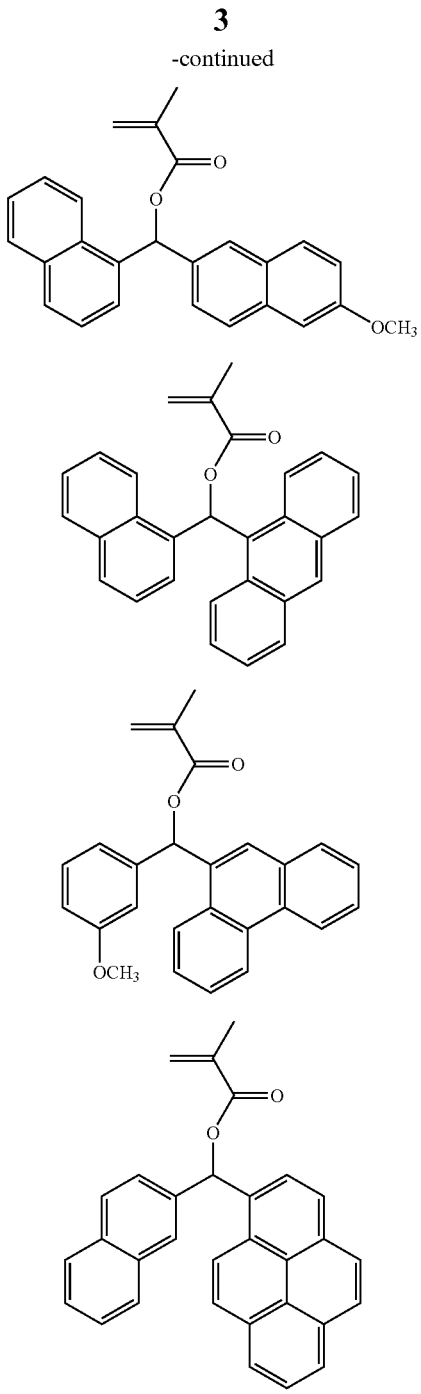

At least one of the above and other features and advantages may also be realized by providing a photosensitive (meth)acrylate polymer, the (meth)acrylate polymer including repeating units represented by Formulae 8a to 8c:

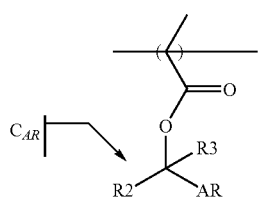

(8a)

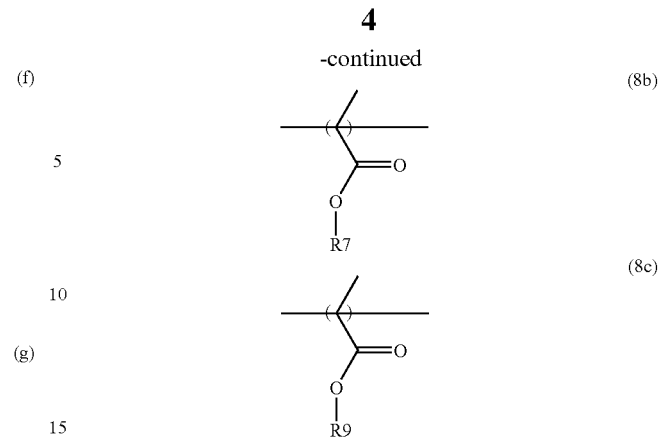

In Formulae 8a to 8c, $R_2$ may be hydrogen, a substituted or unsubstituted alkyl, or a substituted or unsubstituted aryl, $R_3$ may be hydrogen, a substituted or unsubstituted alkyl, or a substituted or unsubstituted aryl, AR may be a substituted or unsubstituted phenyl ring, or a substituted or unsubstituted aryl having from two to four fused aromatic rings, carbon $C_{AR}$ may be bonded directly to an aromatic ring of AR, $R_7$ may be a lactone-derived group or a C4 to C20 acid-labile group, and $R_9$ may be hydrogen, an alkyl including a polar functional group, or a cycloalkyl including a polar functional group where the polar functional group is a hydroxy, a carboxyl, or a combination thereof.

At least one of $R_2$ and $R_3$ may be an alkyl, an alkyl having an alkoxy substituent, an aryl, or an aryl having an alkoxy substituent.

Where $R_7$ is the C4 to C20 acid-labile group, the C4 to C20 acid-labile group may include one or more of norbornyl, isobornyl, cyclodecanyl, adamantyl, norbornyl having a lower alkyl substituent, isobornyl having a lower alkyl substituent, cyclodecanyl having a lower alkyl substituent, adamantyl having a lower alkyl substituent, alkoxycarbonyl, alkoxycarbonylalkyl, arnyloxycarbonyl, amyloxycarbonylalkyl, 2-tetrahydropyranyloxycarbonylalkyl, 2-tetrahydrofuranyloxycarbonylalkyl, a tertiary alkyl, or an acetal.

Where $R_7$ is the lactone-derived group, the lactone-derived group may include at least one of Formulae 4 or 5:

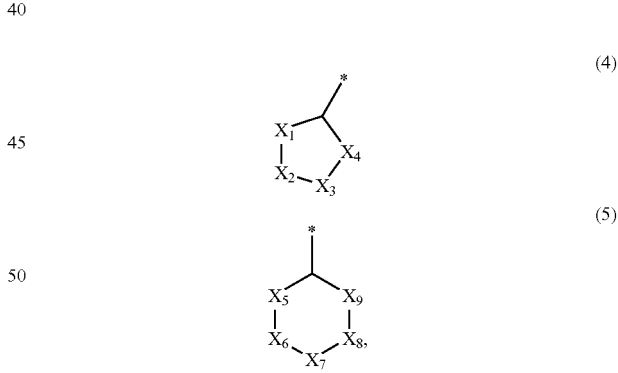

In Formula 4, at least two adjacent groups of $X_1$ to $X_4$ are independently CO and O, and the remaining are CR", where R" is hydrogen, an alkyl, or an alkylene forming a fused ring with the five-member ring, and, in Formula 5, at least two adjacent groups of $X_5$ to $X_9$ may be independently CO and O, and the remaining are CR", where R" is hydrogen, an alkyl, or an alkylene forming a fused ring with the six-member ring, or all of $X_5$ to $X_9$ may be CR'", where R'" is hydrogen, an alkyl, or an ester-containing alkylene forming a fused ring with the six-member ring, and at least two R'" are linked to each other to form a lactone ring.

$R_9$ may be 2-hydroxyethyl or 3-hydroxy-1-adamantyl.

The photosensitive polymer may have a weight average molecular weight of about 3,000 to about 20,000.

The photosensitive polymer may have a polydispersity of about 1.5 to about 2.5.

At least one of the above and other features and advantages may also be realized by providing a resist composition, including a photosensitive (meth)acrylate polymer according to an embodiment, a photoacid generator, and an organic solvent.

The photosensitive (meth)acrylate polymer may be included in an amount of about 5 to about 15 parts by weight, based on 100 parts by weight of the resist composition.

The photoacid generator may be included in an amount of about 1 to about 15 parts by weight, based on 100 parts by weight of the photosensitive (meth)acrylate polymer.

The photoacid generator may include one or more of a triarylsulfonium salt, a diaryliodonium salt, or a sulfonate.

The resist composition may further include an organic base, and the organic base may be present in an amount of about 0.1 to about 1.0 part by weight, based on 100 parts by weight of the photosensitive (meth)acrylate polymer.

The organic base may include one or more of triethylamine, triisobutylamine, trioctylamine, triisodecylamine, or triethanolamine.

At least one of the above and other features and advantages may also be realized by providing a method of patterning a material, the method including forming a resist layer on the material, forming a resist pattern from the resist layer using a lithographic process, and patterning the material through the resist pattern. The resist layer may include a photosensitive (meth)acrylate polymer according to an embodiment.

The lithographic process used to form the pattern in the resist layer may use light having a wavelength of 193 nm or shorter.

BRIEF DESCRIPTION OF THE DRAWINGS

The above and other features and advantages will become more apparent to those of ordinary skill in the art by describing in detail exemplary embodiments with reference to the attached drawings, in which.

DETAILED DESCRIPTION OF THE INVENTION

Figure 1:
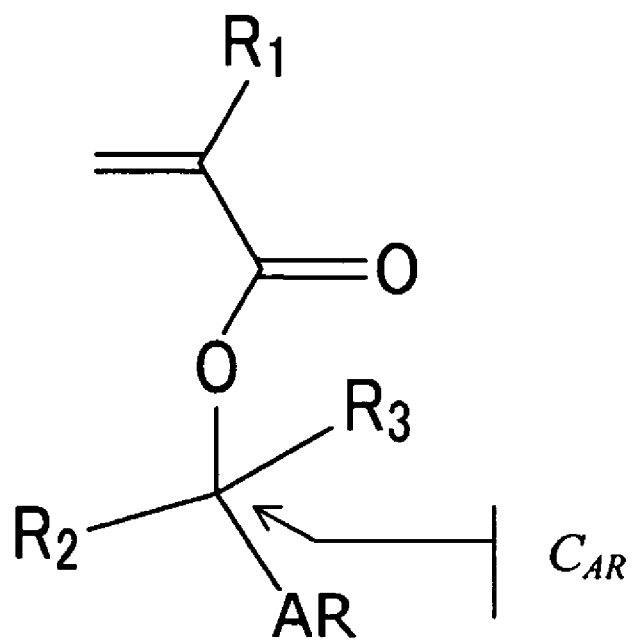
FIG. 1 illustrates Formula 1.
Figure 2:
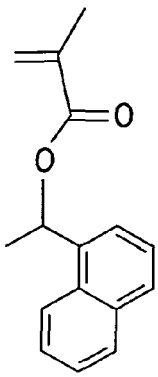
FIG. 2 illustrates Formulae (a)-(i)
Figure 2:
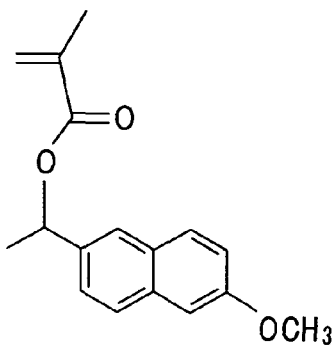
Figure 2:
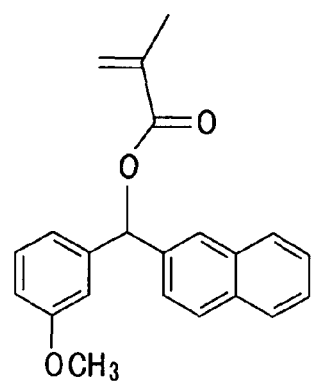
Figure 2:
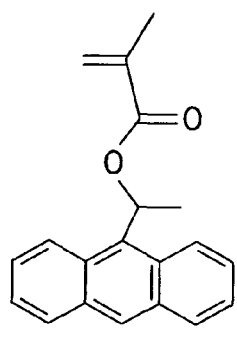
Figure 2:
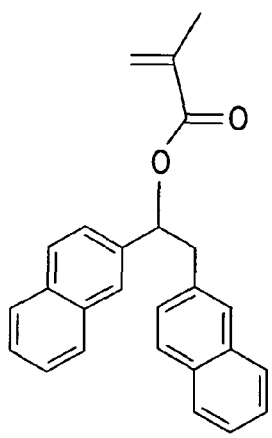
Figure 2:
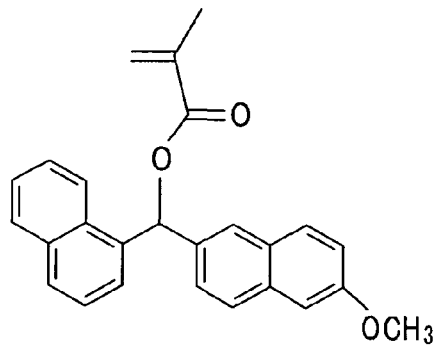
Figure 2:
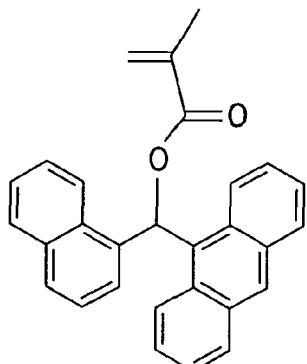
Figure 2:
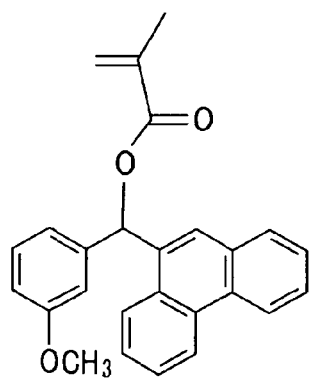
Figure 2:
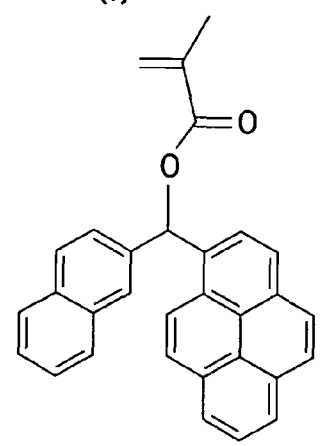
Figure 3:
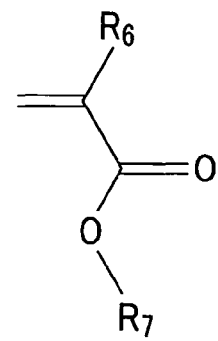
FIG. 3 illustrates Formulae 2-5.
Figure 3:
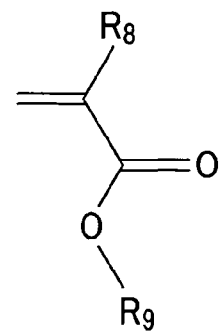
Figure 3:
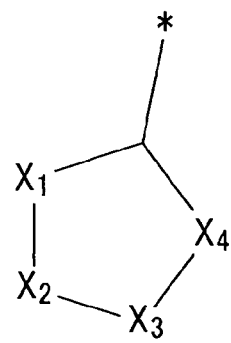
Figure 3:
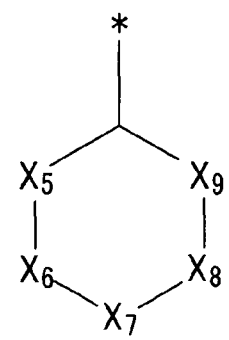
Figure 4:
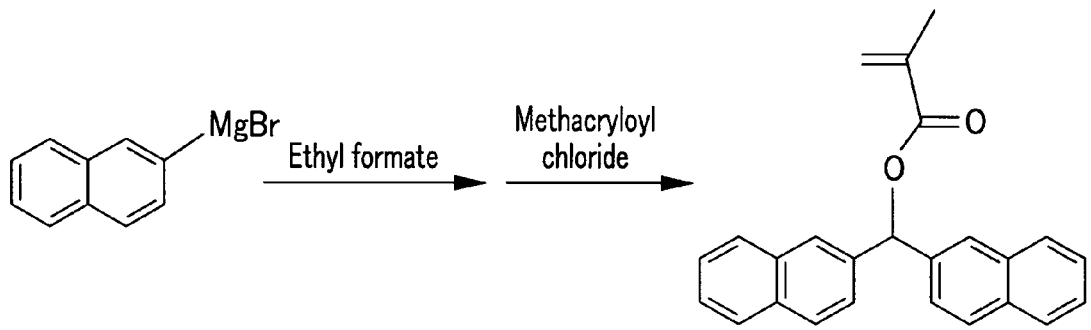
FIG. 4 illustrates Reaction Schemes 1-3.
Figure 4:
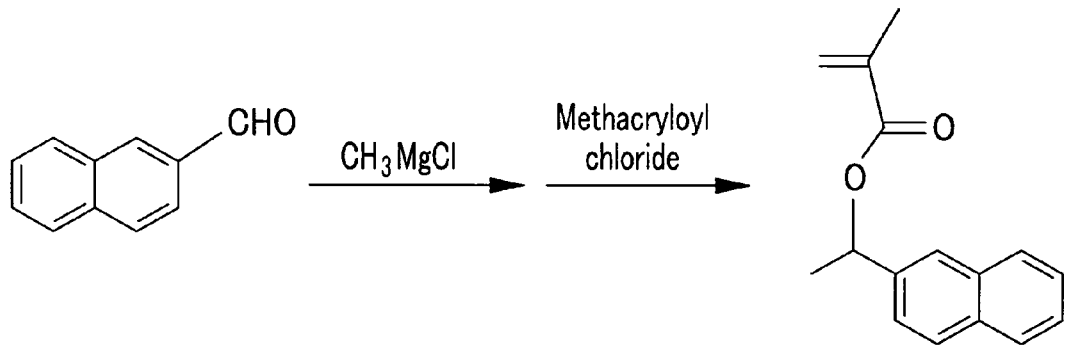
Figure 4:
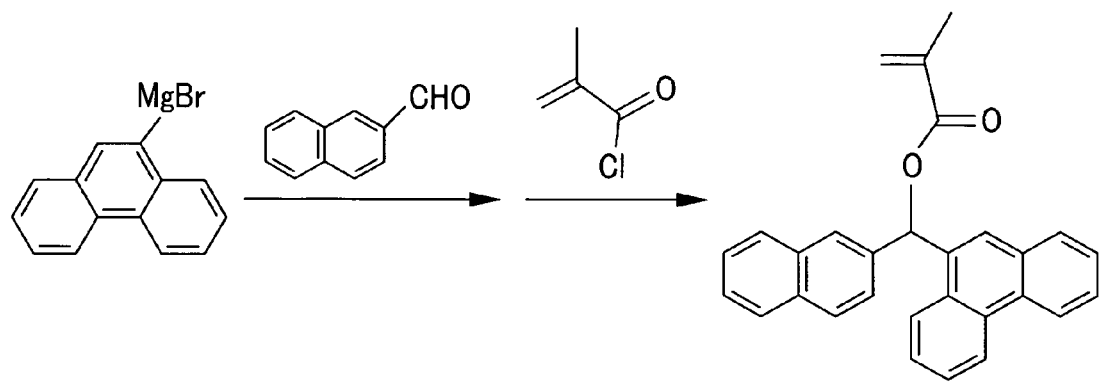
Figure 5:
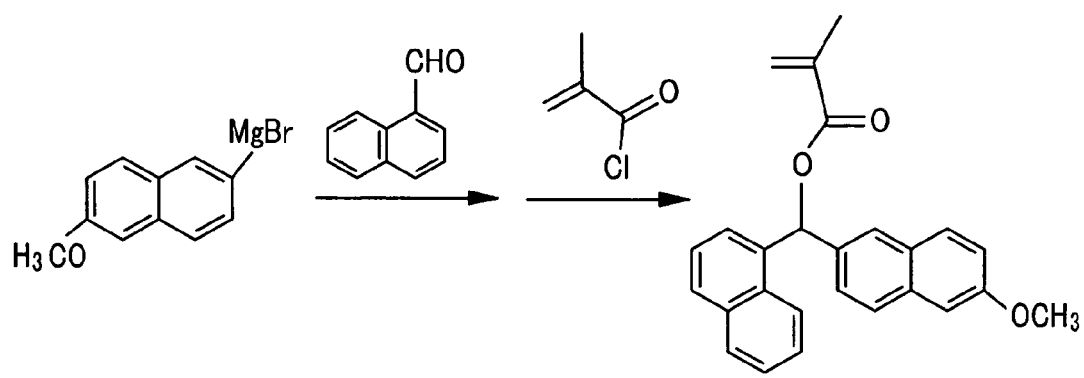
FIG. 5 illustrates Reaction Scheme 4.
Figure 6:
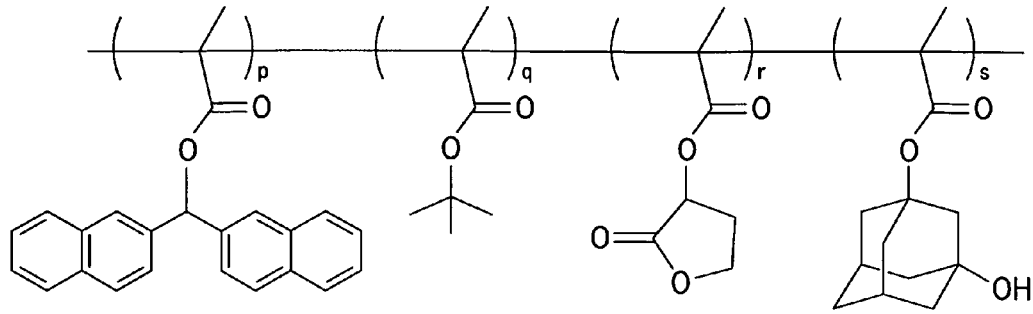
FIG. 6 illustrates Formulae 6-8.
Figure 6:
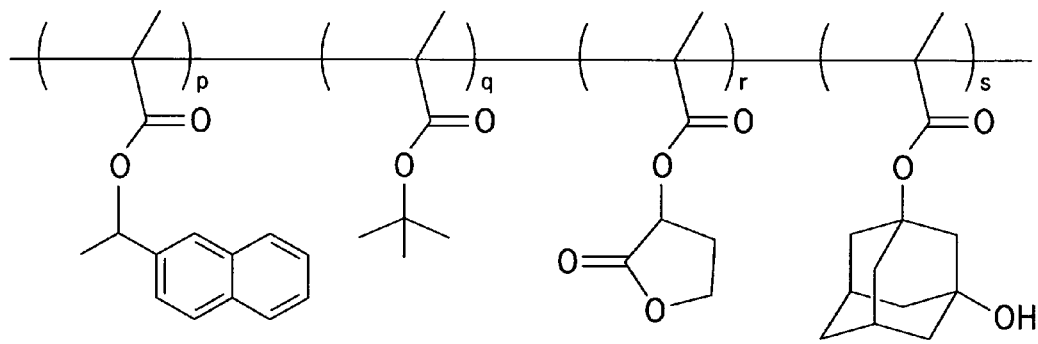
Figure 6:
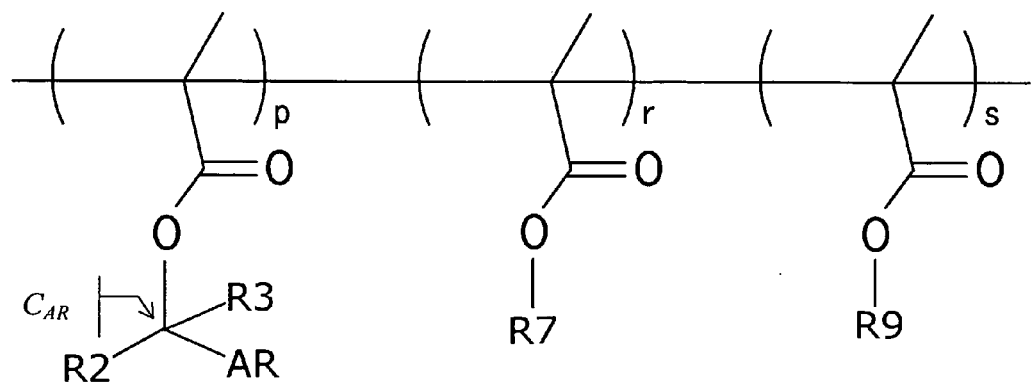

Korean Patent Application No. 10-2007-0132696, filed on Dec. 17, 2007, in the Korean Intellectual Property Office, and entitled: "(Meth)Acrylate Compound and Photosensitive Polymer Having Aromatic Acid Labile Group, and Resist Composition," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art.

As used herein, the expressions "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C" and "A, B, and/or C" includes the following meanings: A alone; B alone; C alone; both A and B together; both A and C together; both B and C together; and all three of A, B, and C together. Further, these expressions are open-ended, unless expressly designated to the contrary by their combination with the term "consisting of." For example, the expression "at least one of A, B, and C" may also include an nth member, where n is greater than 3, whereas the expression "at least one selected from the group consisting of A, B, and C" does not.

As used herein, the expression "or" is not an "exclusive or" unless it is used in conjunction with the term "either." For example, the expression "A, B, or C" includes A alone; B alone; C alone; both A and B together; both A and C together; both B and C together; and all three of A, B, and C together, whereas the expression "either A, B, or C" means one of A alone, B alone, and C alone, and does not mean any of both A and B together; both A and C together; both B and C together; and all three of A, B, and C together.

As used herein, the terms "a" and "an" are open terms that may be used in conjunction with singular items or with plural items. For example, the term "a photoacid generator" may represent a single compound, e.g., triarylsulfonium triflate, or multiple compounds in combination, e.g., triarylsulfonium triflate mixed with 2,6-dinitrobenzyl sulfonate.

As used herein, molecular weights of polymeric materials are weight average molecular weights, unless otherwise indicated.

As used herein, the term "(meth)acrylate" refers to both acrylate and methacrylate. Thus, for example, the term ethyl (meth)acrylate refers to both ethyl acrylate and ethyl methacrylate. Further, the term "acrylate" is generic to both acrylate and methacrylate, unless specified otherwise. Thus, ethyl acrylate and ethyl methacrylate are both acrylates.

As used herein, unless specified otherwise, the term "an alkyl" refers to a C1 to C20 alkyl and preferably a C1 to C12 alkyl, the term "a lower alkyl" refers to a C1 to C4 alkyl, the term "an alkoxy" refers to a C1 to C20 alkoxy and preferably a C1 to C12 alkoxy, the term "an alkylene" refers to a C1 to C20 alkylene and preferably a C1 to C12 alkylene, the term "an aryl" refers to a C6 to C20 aryl and preferably a C6 to C12 aryl, and the term "cycloalkyl" refers to a C3 to C14 cycloalkyl.

Embodiments provide a (meth)acrylate compound having an aromatic acid labile group, a photosensitive polymer, a resist composition, and associated methods. The (meth)acrylate compound may have an aromatic acid-labile group. For example, the (meth)acrylate compound may include aryl groups at various α- or β-positions. The aryl groups may provide the (meth)acrylate compound with dry etching resistance and enable resist contrast control, since the aryls may be easily cleaved. Accordingly, a photosensitive polymer that includes the (meth)acrylate compound according to an embodiment may overcome the drawbacks of known ArF resist materials with respect to dry etching resistance. Thus, the photosensitive polymer according to an embodiment may be useful for forming an etching mask in a process of manufacturing a semiconductor device that requires a high resolution.

According to an embodiment, a (meth)acrylate compound according to an embodiment may be represented by the following Formula 1:

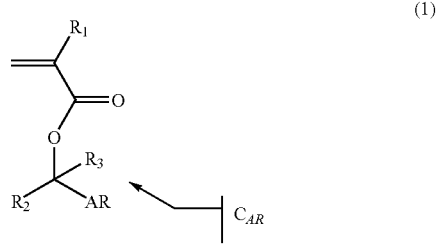

(1)

In Formula 1, $R_1$ may be hydrogen or methyl.
In Formula 1, $R_2$ and $R_3$ may be the same or different, and may independently be hydrogen, a substituted or unsubstituted alkyl, a substituted or unsubstituted aryl, or combinations thereof, and in one embodiment, methyl, ethyl, phenyl, alkyl-phenyl, alkoxy-phenyl, benzyl, naphthyl, alkoxy-naphthyl, naphthalenylmethyl, or combinations thereof.

In Formula 1, AR may include a substituted or unsubstituted phenyl ring. The phenyl ring may be substituted with, e.g., a halogen, an alkyl, or an alkoxy.

In another implementation, AR may include first and second aromatic rings, the first and second aromatic rings being fused together. The first aromatic ring may have a group $R_4$ that is hydrogen, a halogen, an alkyl, or an alkoxy. The second aromatic ring may have a group $R_5$ that is hydrogen, a halogen, an alkyl, or an alkoxy. $R_4$ and $R_5$ may be the same or different. In an implementation, $R_4$ and $R_5$ may independently be a C1 to C6 alkyl or a C1 to C6 alkoxy.

It is preferred that $R_2$ and $R_3$ are not simultaneously hydrogen, i.e., it is preferred that at least one of $R_2$ and $R_3$ is a substituted or unsubstituted alkyl or a substituted or unsubstituted aryl. The substituted alkyl or aryl is preferably substituted with an alkoxy.

The aromatic ring structure AR in Formula 1 may be, e.g., a naphthalene group or an anthracene group. In another implementation, AR may be phenyl. In Formula 1, carbon $C_{AR}$ may be bonded, e.g., directly or indirectly, to an aromatic ring of AR.

Specific examples of the (meth)acrylate compound represented by the above Formula 1 may include compounds represented by the following Formulae (a) to (i):

(a)
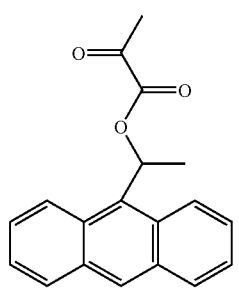

(b)
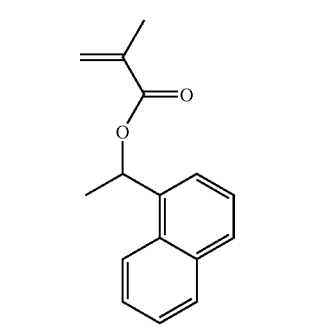

(c)
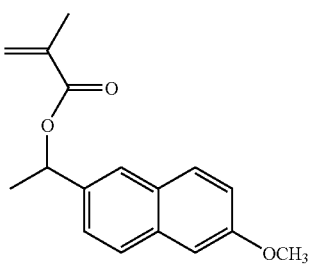

(d)
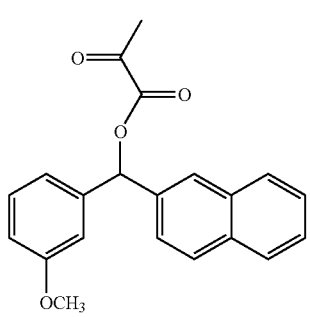

-continued

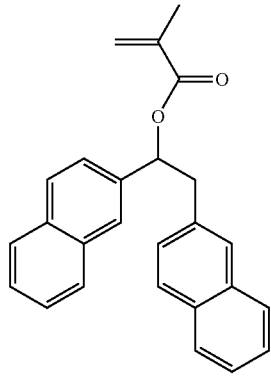

(e)
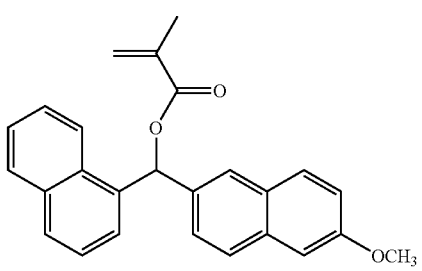

(f)
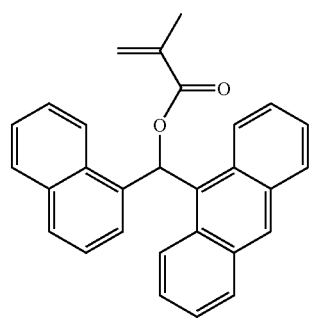

(g)

(h)
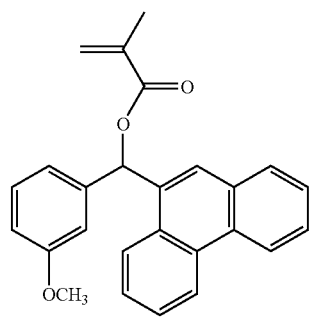

-continued

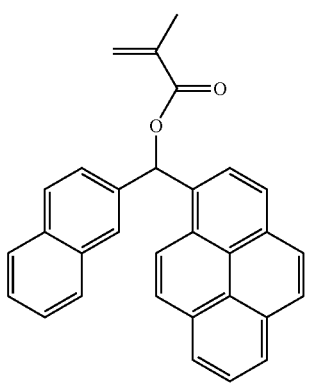

(i)

The (meth)acrylate compound having the aromatic acid-labile group may be synthesized through reactions between various aromatic aldehydes and aromatic Grignard compounds.

According to another embodiment of the present invention, a photosensitive polymer obtained from the (meth)acrylate compound having the aromatic acid-labile group of the above Formula 1 is provided.

In addition to the (meth)acrylate compound having the aromatic acid-labile group of the above Formula 1, the photosensitive polymer may further include repeating units derived from the compounds having the following Formulae 2 and 3:

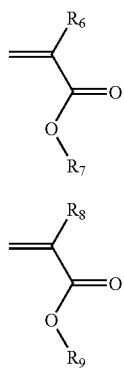

(2)

(3)

In Formulae 2 and 3, $R_6$ and $R_8$ may be the same or different, and may independently be hydrogen or methyl.

In Formula 2, $R_7$ may be a C4 to C20 acid-labile group, which is decomposed under an acid catalyst, or a lactone-derived group.

Where $R_7$ is a C4 to C20 acid-labile group, $R_7$ may include, e.g., norbornyl, isobornyl, cyclodecanyl, adamantyl, norbornyl having a lower alkyl substituent, isobornyl having a lower alkyl substituent, cyclodecanyl having a lower alkyl substituent, adamantyl having a lower alkyl substituent, alkoxycarbonyl, alkoxycarbonylalkyl, amyloxycarbonyl, amyloxycarbonylalkyl, 2-tetrahydropyranyloxycarbonylalkyl, 2-tetrahydrofuranyloxycarbonylalkyl, a tertiary alkyl, an acetal, or combinations thereof. In another embodiment, is 2-methyl-2-norbornyl, 2-ethyl-2-norbornyl, 2-methyl-2-isobornyl, 2-ethyl-2-isobornyl, 8-methyl-8-tricyclodecanyl, 8-ethyl-8-tricyclodecanyl, 2-methyl-2-adamantyl, 2-ethyl-2-adamantyl, 2-propyl-2-adamantyl, t-butoxycarbonyl, t-butoxycarbonylmethyl, t-amyloxycarbonyl, t-amyloxycarbonylmethyl, 1-ethoxyethoxycarbonylmethyl, 2-tetrahydropyranyloxycarbonylalkyl, 2-tetrahydrofuranyloxycarbonylalkyl, t-butyl, triethylcarbyl, 1-methyl cyclohexyl, 1-ethylcyclopentyl, t-amyl, an acetal, or combinations thereof.

Where $R_7$ is the lactone-derived group, $R_7$ may include a substituent represented by Formula 4 or Formula 5 below:

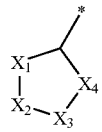

(4)

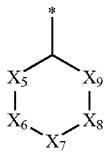

(5)

In Formula 4, at least two adjacent groups of $X_1$ to $X_4$ may independently be CO and O, and the remaining may be CR" (where R" is hydrogen, an alkyl, or an alkylene forming a fused ring with the five-member ring).

In Formula 5, at least two adjacent groups of $X_5$ to $X_9$ may independently be CO and O, and the remaining may be CR" (where R" is hydrogen, an alkyl, or an alkylene forming a fused ring with the six-member ring). In another implementation, all of $X_5$ to $X_9$ may be CR''' (where R''' is hydrogen, an alkyl, or an ester-containing alkylene forming a fused ring with the six-member ring) and at least two R''' are linked to each other to form a lactone ring.

In an embodiment, $R_7$ may be butyrolactonyl, valerolactonyl, 1,3-cyclohexanecarbolactonyl, 2,6-norbornanecarbolacton-5-yl, or 7-oxa-2,6-norbornanecarbolacton-5-yl.

In Formula 3, $R_9$ may be hydrogen, an alkyl including a polar functional group, or a cycloalkyl including a polar functional group. The polar functional group may include a hydroxy, a carboxyl, or a combination thereof. The alkyl may be a C2 to C14 alkyl, and the cycloalkyl may be a C3 to C14 cycloalkyl. Examples of the groups including the polar functional group include: 2-hydroxyethyl, 3-hydroxy-1-adamantyl, and the like.

The photosensitive polymer may be a random copolymer of the (meth)acrylate compound of Chemical Formula 1 having the aromatic acid-labile group, the compound of Chemical Formula 2, and the compound of Chemical Formula 3.

The photosensitive polymer may have an average molecular weight (Mw) of about 3000 to about 20,000.

The photosensitive copolymer may have a polydispersity (ratio of weight average molecular weight to number average molecular weight, i.e., Mw/Mn) of about 1.5 to about 2.5, which may provide excellent etching resistance and resolution.

The photosensitive polymer according to an embodiment may be a copolymer obtained from new functional aromatic acid-labile compounds. Thus, it may provide a resist composition having excellent dry etching resistance compared to a conventional resist material. The (meth)acrylate compounds having aromatic acid-labile groups, such as Formula 1, may be monomers that can be easily decomposed under acid catalysts. Therefore, a photosensitive polymer obtained from the (meth)acrylate compounds according to an embodiment may exhibit improved etching resistance compared to a conventional polymer, such as a conventional polymer having an adamantyl acid-labile group. Further, the photosensitive polymer according to an embodiment may not have a dry etching resistance drawback, unlike a conventional ArF resist material, and, thus, may provide a sufficient etching mask for a semiconductor device requiring a higher resolution. When the resultant resist composition is applied in a photolithographic process, it may provide excellent lithography performance.

According to another embodiment of the present invention, a resist composition including the photosensitive polymer is provided. The resist composition may include the photosensitive polymer according to an embodiment derived from Formula 1, a photoacid generator (PAG), and a solvent. Hereinafter, the components of the resist composition according to an embodiment are described in more detail.

Photosensitive Polymer

The photosensitive polymer is the same as described above, i.e., derived from Formula 1 described above. The photosensitive polymer may be included in an amount of about 5 to about 15 parts by weight, based on 100 parts by weight of the resist composition, which may provide the resist composition with excellent etching resistance and adhesion characteristics.

Photoacid Generator (PAG)

The photoacid generator may include an inorganic onium salt, organic sulfonate, or mixtures thereof. Specific examples of the photoacid generator include sulfonate or iodonium salt including a triarylsulfonium salt, a diaryl iodonium salt, sulfonate, or mixtures thereof. Preferable examples of the photoacid generator include triarylsulfonium triflate, diaryliodonium triflate, triarylsulfonium nonaflate, diaryliodonium nonaflate, succinimidyl triflate, 2,6-dinitrobenzyl sulfonate, or mixtures thereof.

The photoacid generator may be added at about 1 to about 15 parts by weight, based on 100 parts by weight of the photosensitive polymer. Providing about 1 part by weight or more may help ensure that excessive exposure is not required. Providing about 15 parts by weight or less may help avoid decreases in the light transmission of the resist composition.

Solvent

The solvent may include, e.g., propylene glycol monomethyl ether acetate (PGMEA), propylene glycol methyl ether (PGME), ethyl lactate (EL), cyclohexanone, 2-heptanone, etc.

The solvent may be added as the balance amount of the resist composition. In an embodiment, the solvent may be added at 80 to 95 wt % parts by weight, based on 100 parts by weight of the entire resist composition.

Additive

The resist composition may further include an organic base (amine quencher) in order to control the exposure amount and to form a resist profile. The organic base may include, e.g., triethylamine, triisobutylamine, trioctylamine, triisodecylamine, triethanolamine, or mixtures thereof.

The amount of organic base may be about 0.1 to about 1 part by weight, based on 100 parts by weight of the photosensitive polymer. Providing about 0.1 parts by weight or more may help ensure a significant effect. Providing about 1 part by weight or less may help avoid undue increase in the amount of exposure required. Further, excessive organic base may impede pattern formation.

A process for form a pattern using a resist composition according to an embodiment will now be described.

A bare silicon wafer or a silicon wafer including a layer such as a silicon oxide layer, a silicon nitride layer, or a silicon nitride oxide layer on the upper surface thereof may be treated, e.g., with HMDS (hexamethyldisilazane) or an organic anti-reflection coating (bottom anti-reflective coating). Thereafter, the resist composition according to an embodiment may be coated on the silicon wafer to form a resist layer having a thickness of, e.g., about 100 to about 150 nm.

The silicon wafer having the resist layer thereon may be prebaked, e.g., at a temperature of about 90 to 120° C. for about 60 to 90 seconds, to remove solvent. A resist pattern may be formed from the resist layer using a process that includes, e.g., exposure to an exposure light source. The light source may be, e.g., ArF or a shorter wavelength, e.g., EUV (extreme UV), E-beam, and so on. In order to drive the chemical reaction in the exposed region of the resist layer, the layer may be subjected to PEB (post-exposure baking), e.g., at a temperature of about 90 to 120° C. for about 60 to 90 seconds.

Then the resist layer may be developed, e.g., in a basic aqueous developing solution such as a TMAH (tetramethylammonium hydroxide) solution. The exposed region may have a very high solubility in the basic aqueous developing solution, so it may be easily dissolved and removed during the development. When the exposure light source is an ArF excimer laser, an 80 to 100 nm line and space pattern may be produced at an exposure dose of about 5 to about 50 mJ/cm2.

The resist pattern obtained from the above lithographic process may be used as a mask to pattern an underlying layer, e.g., an underlying silicon oxide layer, by using an etchant, e.g., a plasma of halogen gas or $C_xF_y$ gas such as a perfluorinated alkane in which x is a positive integer and y=2x+2. The resist pattern that remains on the wafer may then be removed by using a stripper to yield a desired pattern in the target material layer, e.g., a silicon oxide layer pattern.

The following examples are provided in order to set forth particular details of one or more example embodiments. However, it will be understood that the embodiments described herein are not limited to the particular details described in the examples.

Example 1-1

Synthesis of bis(2-naphthyl)methyl Methacrylate Monomer

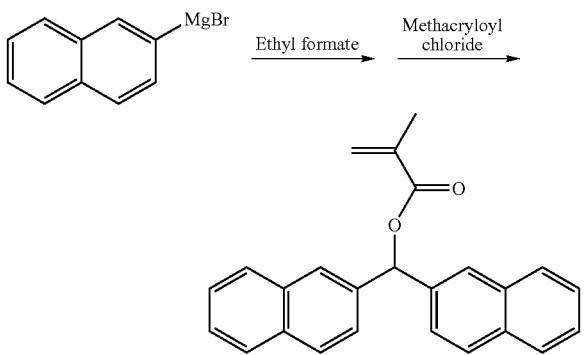

Using the method shown in Reaction Scheme 1, a bis(2-naphthyl)methyl methacrylate monomer was synthesized as follows:

3.5 g of ethyl formate was dissolved in 50 mL of THF in a round bottom flask, and 200 mL of a 2-naphthyl magnesium bromide solution (0.5 M in THF) was slowly added in a dropwise fashion. The resulting mixture was reacted at about 40° C. for about 2 hours. After the reaction, the obtained reactant was dropped in an extreme amount of water and then, neutralized with thin hydrochloric acid. The resulting product was extracted with diethyl ether. The extract was purified through column chromatography using hexane and methylene chloride mixed in a ratio of 2:1.

14 g of the acquired product and 5 g of TEA (triethylamine) were dissolved in 200 mL of THF, and 6 g of methacryloyl chloride was slowly added in a dropwise fashion. The mixture was reacted at a room temperature for 4 hours. After the reaction, the acquired reaction product was put in an extreme amount of water and extracted using diethyl ether. The extract was purified through column chromatography using hexane and ethyl acetate mixed in a ratio of 3:1, obtaining a bis(2-naphthyl)methyl methacrylate monomer (yield: 50%).

¹H-NMR (CDCl₃, ppm): 8.0 (m, 6H, aromatic), 7.6 (m, 6H, aromatic), 7.2 (m, 2H, aromatic), 6.5 (s, 1H, —CH—), 6.4 (m, 2H, vinyl), 1.9 (s, 3H, —CH₃).

Example 1-2

Synthesis of a 1-(naphthalen-2-yl)ethyl Methacrylate Monomer

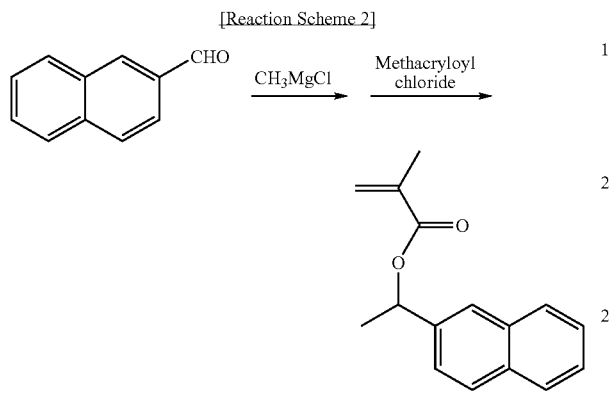

[Reaction Scheme 2]

Using the method shown in Reaction Scheme 2, a 1-(naphthalen-2-yl)ethyl methacrylate monomer was synthesized according to the same method as Example 1-1, except for using methyl magnesium chloride instead of 2-naphthyl magnesium bromide, and using 2-naphthaldehyde instead of ethyl formate (yield: 50%).

Example 1-3

Synthesis of a naphthalen-2-yl(phenanthren-9-yl)methyl Methacrylate) monomer

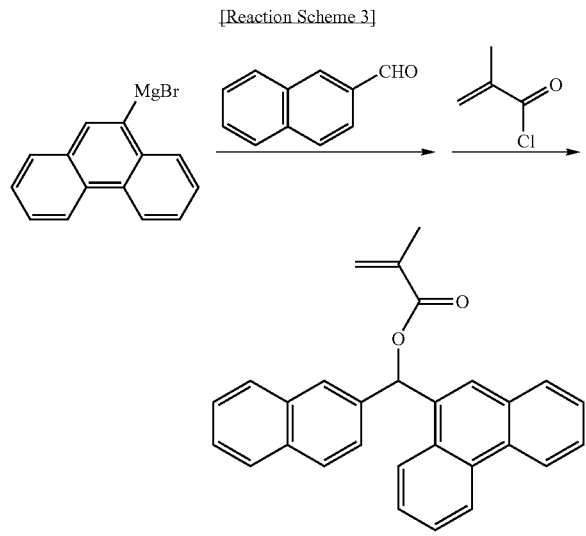

[Reaction Scheme 3]

Using the method shown in Reaction Scheme 3, a naphthalen-2-yl(phenanthren-9-yl)methyl methacrylate monomer was synthesized according to the same method as Example 1-1, except for using 9-phenanthrenyl magnesium bromide instead of 2-naphthyl magnesium bromide, and using 2-naphthaldehyde instead of ethyl formate (yield: 40%).

Example 1-4

Synthesis of a (6-methoxynaphthalen-2-yl)(naphthalen-1-yl)methyl Methacrylate) Monomer

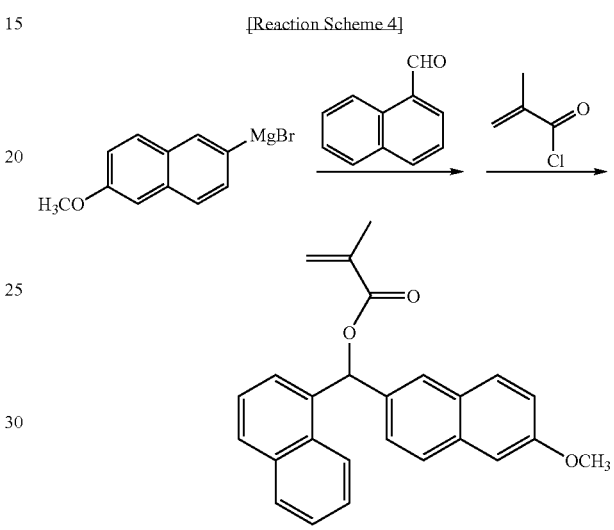

[Reaction Scheme 4]

Using the method shown in Reaction Scheme 4, a (6-methoxynaphthalen-2-yl) (naphthalen-1-yl)methyl methacrylate monomer was synthesized according to the same method as Example 1-1, except for using 6-methoxynaphthalen-2-yl) magnesium bromide instead of 2-naphthyl magnesium bromide, and using 1-naphthaldehyde instead of ethyl formate (yield: 40%).

Example 2-1

Synthesis of a Photosensitive Polymer 20 mmol of the monomer of Example 1-1, 20 mmol of t-butyl methacrylate, 40 mmol of γ-butyrolactonyl methacrylate (GBLMA), and 20 mmol of 3-hydroxy-1-adamantyl methacrylate (HAMA) were put in a round flask and dissolved in a methylethyl ketone (MEK) solvent (four times based on the entire weight of the monomer), and dimethyl-2,2'-azobis (2-methylpropionoate) (V601, Wako Pure Chemical Industries Ltd.) as a polymerization initiator was added thereto. The resulting product was stored with N₂ gas for about 30 minutes and then polymerized at 80° C. for 4 hours.

After the polymerization, the reactant was slowly precipitated in a large amount of diethyl ether solvent. The precipitate was filtered, then redissolved in a predetermined amount of THF, and then reprecipitated in diethyl ether. The resultant precipitate was dried in a 50° C. vacuum oven for about 24 hours, obtaining a polymer represented by the following Formula 6 (yield: 55%). The polymer had a weight average molecular weight (Mw) of 14,800 and a polydispersity (Mw/Mn) of 1.8.

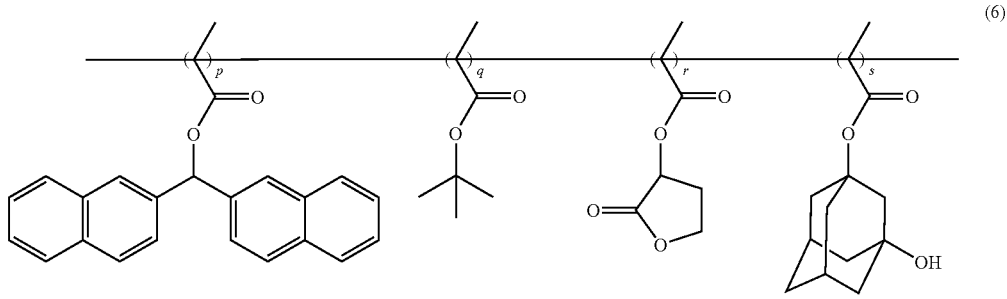

(6)

In Formula 6, p=20, q=20, r=40, and s=20.

Example 2-2

Synthesis of a Photosensitive Polymer 20 mmol of the monomer of Example 1-2, 20 mmol of t-butyl methacrylate, 40 mmol of γ-butyrolactonyl methacrylate (GBLMA), and 20 mmol of 3-hydroxy-1-adamantyl methacrylate (HAMA) were put in a round flask and dissolved in a methyl ethyl ketone solvent (four times based on the entire amount of the monomer), and 5 mmol of V601 (Wako Pure Chemical Industry Ltd.) was added thereto. The mixture was polymerized according to the same method as Example 2-1, obtaining a polymer represented by the following formula 7 (yield: 60%). The polymer had a weight average molecular weight (Mw) of 13,600 and a polydispersity (Mw/Mn) of 1.8.

organic BARC ($AR_46$, manufactured by Rohm and Hass) had previously been formed in a thickness of 600 Å and pre-baked at 110° C. (soft baking: SB) for 60 seconds. The resist layer was exposed to an ArF scanner (0.78 NA, dipole). PEB (post-exposure baking) was carried out at 110° C. for 60 seconds, and the exposed resist layer was developed in a 2.38 wt % TMAH solution for 60 seconds. As a result, a clear 100 nm L/S (line and space) pattern was obtained.

Experimental Example 2

Etching Resistance Evaluation

The photosensitive polymer of Example 2-1 was evaluated as to etching characteristics in a RIE (reactive ion etching) method by measuring bulk etching under $CF_4$ gas condition (composition: power 100 W, pressure 5 Pa, flow rate 30 ml/min). The etching rate of a poly(hydroxystyrene) polymer,

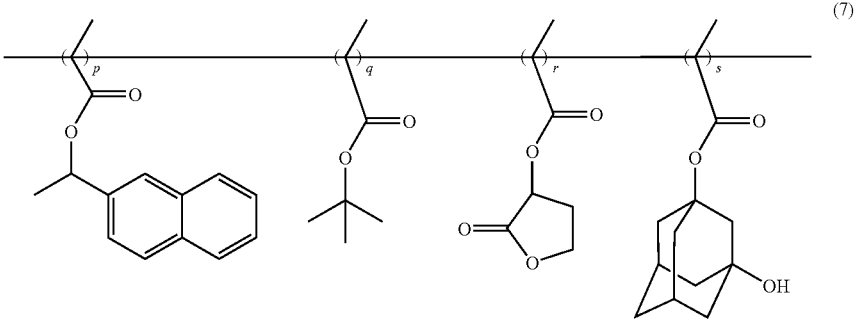

(7)

In Formula 7, p=20, q=20, r=40, and s=20.

Example 3

Preparation of Resist Composition and Lithography Performance 1 g of the photosensitive polymer according to Example 2-1 was dissolved in 17 g of PGMEA/EL (6/4) together with triphenylsulfonium (TPS) nonaflate PAG (0.02 g). An organic base of triethanolamine (1 mg) was added thereto and completely dissolved.

Experimental Example 1

Resolution Evaluation

The resist solution according to Example 3 was filtered with a 0.1 μm membrane filter. The filtered resist solution was coated at a thickness of 140 nm on a silicon wafer to which an typically used as a resist for KrF, was used as a reference for normalization of the measurement. Based on this characterization, the photosensitive polymer of Example 2-1 had about 1.10 times faster etching rate than a polymer for KrF.

As described above, a (meth)acrylate compound according to an embodiment may be used to form a photosensitive polymer having excellent adhesion characteristics to an underlying layer, and providing excellent dry etching resistance during a lithographic process. The resist composition including the photosensitive polymer according to an embodiment may provide excellent lithography performance in a lithographic process using an ultrashort wavelength region, such as a 193 nm region or EUV (13.5 nm) region light source. Further, the (meth)acrylate compound may be easily prepared at a low cost.

A photosensitive polymer obtained from the monomeric (meth)acrylate compound having an aromatic acid-labile group according to an embodiment may exhibit excellent dry etching resistance, and may control resist contrast through an aromatic substituent that undergoes a decomposition reaction under an acid catalyst. In addition, a resist composition including the photosensitive polymer according to an embodiment may have a better dry etching characteristic than a conventional ArF resist material, and may exhibit excellent adherence to an underlayer. Therefore, it may be very useful for fabricating next-generation semiconductors.

Example embodiments have been disclosed herein, and although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A methacrylate compound having an aromatic acid-labile group, the methacrylate compound being represented by one of the following structures (c), (e), (f), (g), (h), or (i):

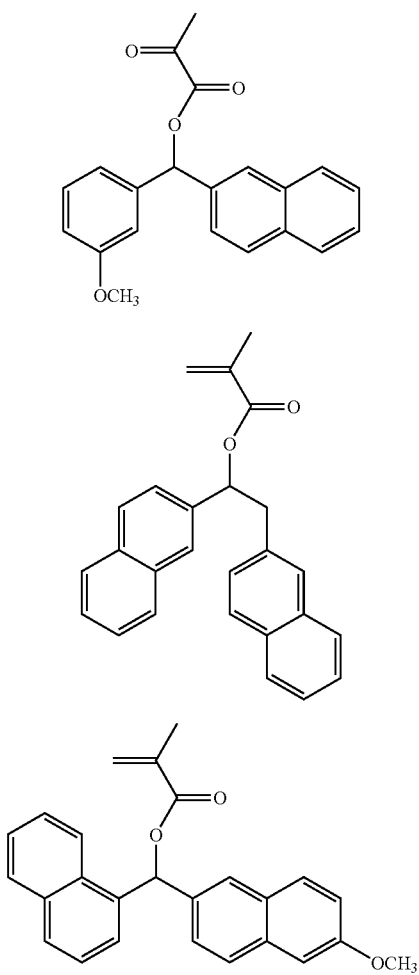

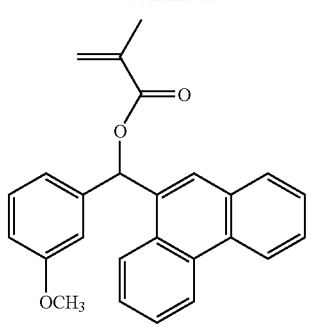

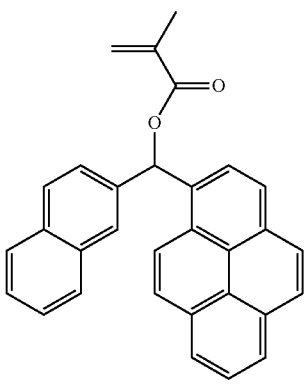

2. A photosensitive methacrylate polymer, comprising:
repeating units represented by Formulae 8b and 8c:

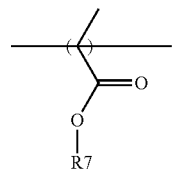

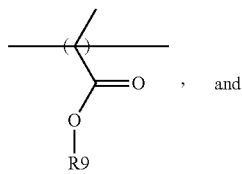

repeating units represented by one of the following structures (cl), (el), (fl), (gl), (hl), or (il):

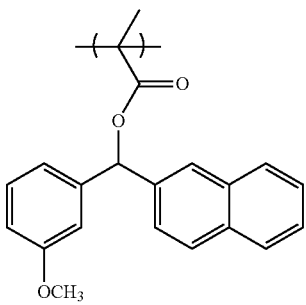

-continued (e1) 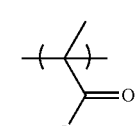

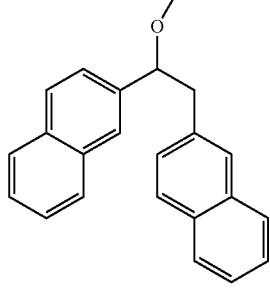

(f1) 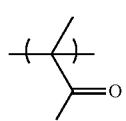

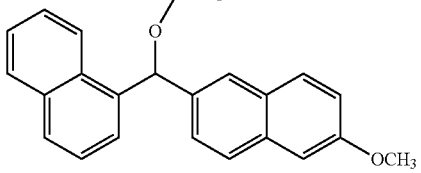

(g1) 

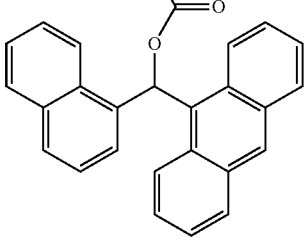

(h1) 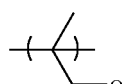

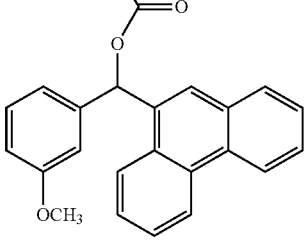

(i1) 

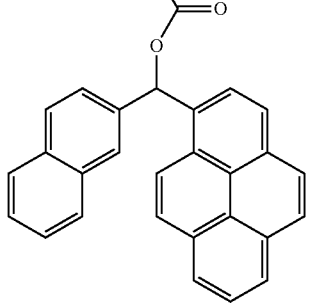

wherein, in Formulae 8b and 8c:
$R_7$ is a lactone-derived group or a C4 to C20 acid-labile group, and
$R_9$ is hydrogen, an alkyl including a polar functional group, or a cycloalkyl including a polar functional group where the polar functional group is a hydroxy, a carboxyl, or a combination thereof.

3. The photosensitive polymer as claimed in claim 2, wherein:
$R_7$ is the C4 to C20 acid-labile group, and
the C4 to C20 acid-labile group includes one or more of norbornyl, isobornyl, cyclodecanyl, adamantyl, norbornyl having a lower alkyl substituent, isobornyl having a lower alkyl substituent, cyclodecanyl having a lower alkyl substituent, adamantyl having a lower alkyl substituent, alkoxycarbonyl, alkoxycarbonylalkyl, amyloxycarbonyl, amyloxycarbonylalkyl, 2-tetrahydropyranyloxycarbonylalkyl, 2-tetrahydrofuranyloxycarbonylalkyl, a tertiary alkyl, or an acetal.

4. The photosensitive polymer as claimed in claim 2, wherein:
$R_7$ is the lactone-derived group,
the lactone-derived group includes at least one of Formulae 4 or 5:

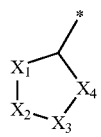

(4)

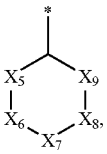

(5)

in Formula 4, at least two adjacent groups of $X_1$ to $X_4$ are independently CO and O, and the remaining are CR", where R" is hydrogen, an alkyl, or an alkylene forming a fused ring with the five-member ring, and
in Formula 5:
at least two adjacent groups of $X_5$ to $X_9$ are independently CO and O, the remaining are CR", where R" is hydrogen, an alkyl, or an alkylene forming a fused ring with the six-member ring, or
all of $X_5$ to $X_9$ are CR'", where R'" is hydrogen, an alkyl, or an ester-containing alkylene forming a fused ring with the six-member ring, and at least two R'" are linked to each other to form a lactone ring.

5. The photosensitive polymer as claimed in claim 2, wherein $R_9$ is 2-hydroxyethyl or 3-hydroxy-1-adamantyl.

6. The photosensitive polymer as claimed in claim 2, wherein the photosensitive polymer has a weight average molecular weight of about 3,000 to about 20,000.

7. The photosensitive polymer as claimed in claim 2, wherein the photosensitive polymer has a polydispersity of about 1.5 to about 2.5.

8. A resist composition, comprising:
a photosensitive methacrylate polymer as claimed in claim 2;
a photoacid generator; and
an organic solvent.

9. The resist composition as claimed in claim 8, wherein the photosensitive methacrylate polymer is included in an amount of about 5 to about 15 parts by weight, based on 100 parts by weight of the resist composition.

10. The resist composition as claimed in claim 8, wherein the photoacid generator is included in an amount of about 1 to about 15 parts by weight, based on 100 parts by weight of the photosensitive methacrylate polymer.

11. The resist composition as claimed in claim 8, wherein the photoacid generator includes one or more of a triarylsulfonium salt, a diaryliodonium salt, or a sulfonate.

12. The resist composition as claimed in claim 8, further comprising an organic base, wherein the organic base is present in an amount of about 0.1 to about 1.0 part by weight, based on 100 parts by weight of the photosensitive methacrylate polymer.

13. The resist composition as claimed in claim 12, wherein the organic base includes one or more of triethylamine, triisobutylamine, trioctylamine, triisodecylamine, or triethanolamine.

14. A method of patterning a material, the method comprising:
    forming a resist layer on the material;
    forming a resist pattern from the resist layer using a lithographic process; and
    patterning the material through the resist pattern, wherein:
    the resist layer includes a photosensitive methacrylate polymer, the methacrylate polymer including:
    repeating units represented by Formulae 8b and 8c:

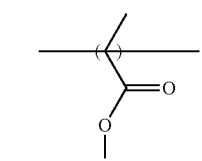
(8b)

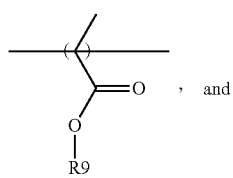
(8c)

and repeating units represented by one of the following structures (cl), (el), (fl), (gl), (hl), or (il):

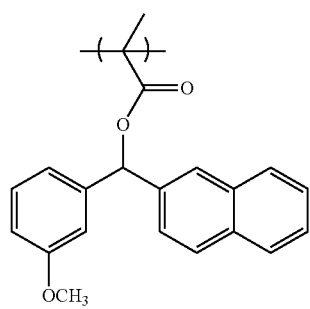
(cl)

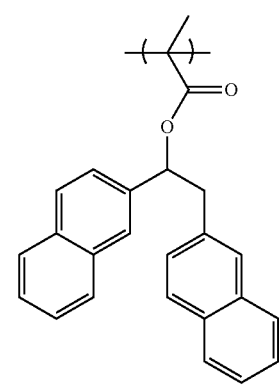
(el)

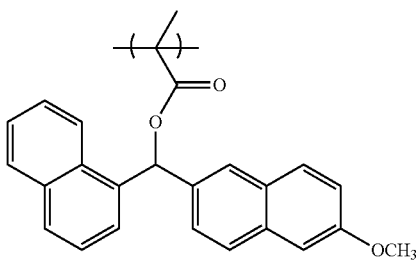
(fl)

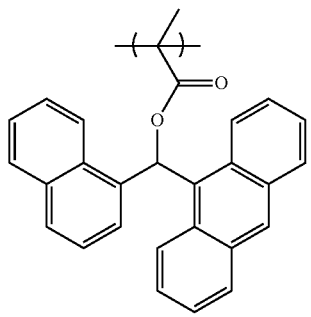
(gl)

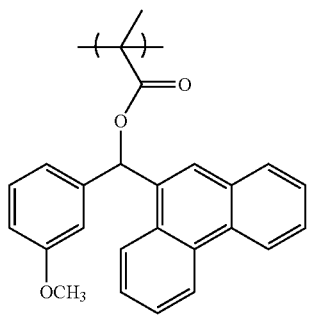
(hl)

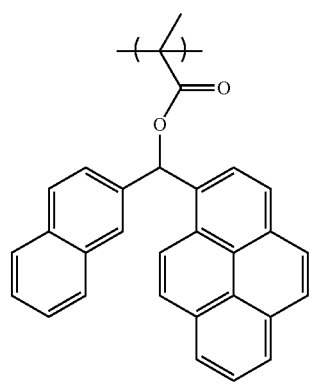
(il)

wherein, in Formulae 8b and 8c:
    $R_7$ is a lactone-derived group or a C4 to C20 acid-labile group, and
    $R_9$ is hydrogen, an alkyl including a polar functional group, or a cycloalkyl including a polar functional group where the polar functional group is a hydroxy, a carboxyl, or a combination thereof.

15. The method as claimed in claim 14, wherein the lithographic process used to form the pattern in the resist layer uses light having a wavelength of 193 nm or shorter.

* * * * *